(12) United States Patent
Lizauckas et al.

(10) Patent No.: US 10,470,812 B2
(45) Date of Patent: Nov. 12, 2019

(54) FILTRATION DEVICE FOR CENTRAL VACUUM SYSTEM

(71) Applicant: Buffalo Filter LLC, Lancaster, NY (US)

(72) Inventors: Anthony Lizauckas, Williamsville, NY (US); Kyrylo Shvetsov, Depew, NY (US); Gregory Pepe, Lancaster, NY (US); Daniel R. Palmerton, Elma, NY (US)

(73) Assignee: Buffalo Filter LLC, Lancaster, NY (US)

( * ) Notice: Subject to any disclaimer, the term of this patent is extended or adjusted under 35 U.S.C. 154(b) by 108 days.

(21) Appl. No.: 15/508,810

(22) PCT Filed: Sep. 8, 2015

(86) PCT No.: PCT/US2015/048890
§ 371 (c)(1),
(2) Date: Mar. 3, 2017

(87) PCT Pub. No.: WO2016/040286
PCT Pub. Date: Mar. 17, 2016

(65) Prior Publication Data
US 2017/0245908 A1    Aug. 31, 2017

Related U.S. Application Data

(60) Provisional application No. 62/047,322, filed on Sep. 8, 2014.

(51) Int. Cl.
*B01D 46/00*    (2006.01)
*B01D 50/00*    (2006.01)
(Continued)

(52) U.S. Cl.
CPC ........... *A61B 18/00* (2013.01); *A61M 1/0035* (2014.02); *A61M 1/0043* (2013.01);
(Continued)

(58) Field of Classification Search
CPC ........ A61B 18/00; B01D 46/00; B01D 50/00; B01D 46/0086; B01D 46/429; B01D 46/46; B01D 50/006
(Continued)

(56) References Cited

U.S. PATENT DOCUMENTS

| 5,597,385 A | 1/1997 | Moerke |
| 6,045,596 A * | 4/2000 | Holland, Jr. ........... B01D 46/00 55/385.2 |

(Continued)

OTHER PUBLICATIONS

International Search Report and Written Opinion of The International Searching Authority (6 pages) dated Jan. 13, 2016.

*Primary Examiner* — Robert A Hopkins
(74) *Attorney, Agent, or Firm* — Timothy W. Menasco; Harter Secrest & Emery, LLP

(57) ABSTRACT

A filtration system for use in connection with a central vacuum system in a hospital or other medical facility. In certain aspects, the filtration system comprises a removable filter for removing contaminants; a fitting adapted for connection to a central vacuum source/system which provides constant suction, which fitting is positioned between the filter and the central vacuum source; a flow control valve positioned between the filter and the fitting; wherein the relative positions of the fitting, flow valve and filter prevent contaminants from being discharged into the central vacuum system. In other aspects, the system provides variable filter life based upon variable flow.

10 Claims, 7 Drawing Sheets

(51) Int. Cl.
  *A61B 18/00* (2006.01)
  *B01D 46/46* (2006.01)
  *B01D 46/42* (2006.01)
  *A61M 1/00* (2006.01)
  *A61M 27/00* (2006.01)
  *A61M 39/22* (2006.01)

(52) U.S. Cl.
  CPC ........ *A61M 1/0052* (2014.02); *A61M 1/0056* (2013.01); *B01D 46/00* (2013.01); *B01D 46/0086* (2013.01); *B01D 46/429* (2013.01); *B01D 46/46* (2013.01); *B01D 50/006* (2013.01); *A61B 2218/008* (2013.01); *A61M 1/0023* (2013.01); *A61M 1/0029* (2014.02); *A61M 1/0031* (2013.01); *A61M 1/0049* (2013.01); *A61M 27/00* (2013.01); *A61M 39/22* (2013.01)

(58) Field of Classification Search
  USPC ........... 55/385.1; 96/417; 604/319, 322, 902
  See application file for complete search history.

(56) References Cited

U.S. PATENT DOCUMENTS

| | | | |
|---|---|---|---|
| 6,391,102 B1 | 5/2002 | Bodden et al. | |
| 7,597,731 B2 * | 10/2009 | Palmerton | A61B 18/00 55/385.1 |
| 2005/0060974 A1 | 3/2005 | Palmerton et al. | |
| 2009/0221963 A1 | 9/2009 | Lloyd et al. | |
| 2010/0139659 A1 | 6/2010 | Von Blumenthal | |
| 2012/0286179 A1 * | 11/2012 | Palmerton | G05B 19/0423 251/129.04 |

* cited by examiner

FILTRATION DEVICE FOR CENTRAL VACUUM SYSTEM

PRIORITY CLAIM

The present application claims priority to U.S. Provisional Patent Application No. 62/047,322, filed Sep. 8, 2014.

BACKGROUND OF THE INVENTION

The present invention relates generally to filtration devices and systems for use in connection with medical procedures and, more specifically, for use in connection with a central vacuum system in a hospital or other medical facility.

BRIEF SUMMARY OF THE INVENTION

With reference to the corresponding parts, portions or surfaces of the disclosed embodiment, merely for the purposes of illustration and not by way of limitation, the present invention provides an improved filtration device and system for use in an operating room (OR) boom (1), OR wall (1), suite or cart, with a filter basket comprising a filter (6) and a filter receiver (5) configured and arranged to receive input through tubing (9) from a surgical site. In one aspect, a connector (3) such as a pipe fitting or barbed fitting is provided between the filter basket (5, 6) and the hospital's or medical facility's central vacuum source (2). In one embodiment, the tubing (9) and filter (6) are connected, configured and arranged such that the filter is close to the surgical site (i.e. the filter is not positioned such that smoke, blood and contaminants are discharged into the central vacuum source and associated piping/tubing, which would require cleaning/maintenance/replacement).

In another aspect, the filtration system/device comprises a valve (4) such as a solenoid valve or the like for turning flow on and off, for throttling (or limiting) flow, or for counting or determining filter life, for example. In one aspect, the filtration system provides constant suction from the central vacuum source (2) but also provides the hospital or medical provider with the option to stop or limit airflow (on/off and variable switching/flow) through the tubing (i.e. bypass) with such a valve.

In another embodiment, the invention provides variable filter life based on variable flow. For example, if the strength of the vacuum is limited to 50% of available flow from the central vacuum source, the determination of filter life is adjusted accordingly (in this example, the filter life would be decremented at 50% of time during the period of 50% flow).

The filtration system/device may also comprise a control panel (7) for controlling the valve or solenoid. In one aspect, the control panel (7) provides various methods of remote activation such as RF, Bluetooth or wireless, for example (and any method, system or apparatus disclosed in U.S. Provisional Patent Application No. 61/431,492, filed Jan. 11, 2011, U.S. Provisional Patent Application No. 61/579,937, filed Dec. 23, 2011, or U.S. patent application Ser. No. 13/348,630, filed Jan. 11, 2012, all of which are incorporated herein by reference).

For example, a remote control unit may be provided comprising: an receiver having an output; an output control line for controlling a device; a threshold setting button; a threshold parameter storage; a controller, configured to store a threshold parameter into the threshold parameter storage when the threshold setting button may be depressed, the threshold parameter being a function of the receiver output; and in which the controller is configured to produce a signal on the output control line as a function of the receiver output and the threshold parameter storage.

The receiver may be a RF receiver, and may be a Bluetooth, or WiFi IEEE 802.11) transceiver. The receiver may be an acoustic receiver. The output control line may be a digital wire whereby a first voltage on the output control line may be used to identify when the device is turned on and a second voltage on the output control line may be used to identify when the device is turned off. The RF receiver may comprise an antenna. The antenna may be an integrated antenna.

In another aspect, the filtration system and device may be configured and arranged to connect an electrosurgical generator, laser or plasma knife into an outlet near the device to sense activation of a plume-producing surgical instrument (e.g. sensing of power consumption on the electrical power line, or sensing RF energy generated during activation).

In another embodiment, an oxygen sensor is provided to determine $O_2$ concentration at the surgical site. In one aspect, the system is configured and arranged to increase flow based on $O_2$ levels and, in another aspect, to limit activation of a generator or laser plugged into a dedicated outlet.

DETAILED DESCRIPTION OF THE PREFERRED EMBODIMENTS

Figure 1:
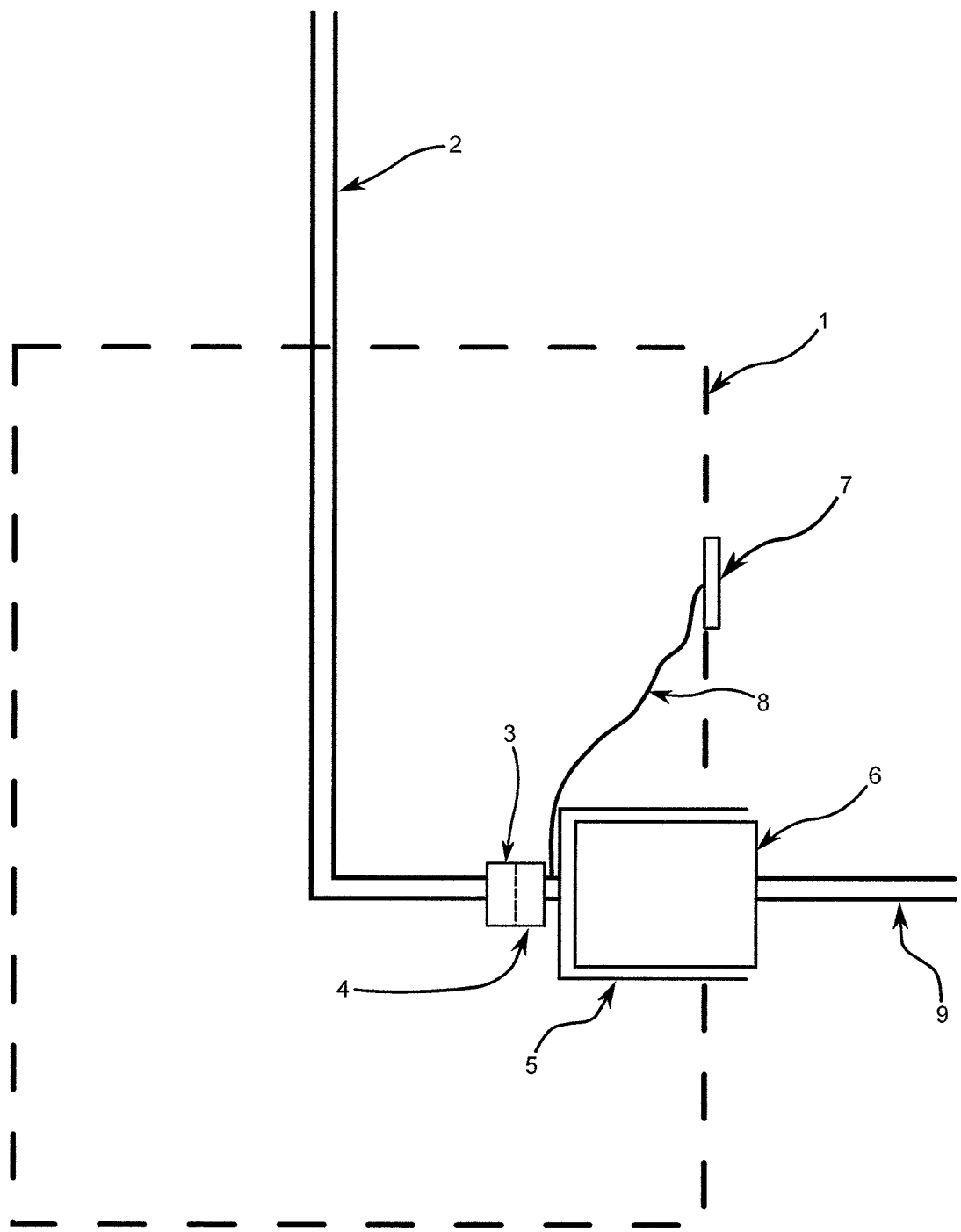
FIG. 1 shows a schematic view of a first embodiment of a filtration device.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, FIG. 1 is an embodiment of a filtration system and device for use in a hospital or medical facility with a central vacuum system. In this embodiment, the filtration system/device is mounted in or associated with an OR boom or wall 1. It may also be mounted or incorporated in a suite or cart known to those skilled in the art. A central vacuum source 2 is provided which is connected through a connector 3 to a filter receiver 5 and filter 6 (collectively, a filter basket). The filter basket permits insertion and removal of filters and replacement filters as desired. This embodiment also includes a valve 4 such as a solenoid valve for controlling air flow to/from the surgical site. The filter basket (filter 6 and filter receiver 5) is connected through tubing 9 to the surgical site. A control panel 7 is also provided, said control panel being electrically connected to the filtration device through an electrical connection 8.

The filter basket 5, 6 in this embodiment is positioned near the surgical site such that smoke, blood and contaminants are filtered near the surgical site to eliminate or minimize the smoke, blood and contaminants which are transmitted to the central vacuum system 2 and associated piping and tubing.

The filtration system and device may be configured and arranged to connect an electrosurgical generator, laser or plasma knife (not shown) into an outlet near the device to sense activation of a plume-producing surgical instrument in a manner described below or known to those skilled in the art (e.g. sensing of power consumption on the electrical power line, or sensing RF energy generated during activation).

Figure 2:
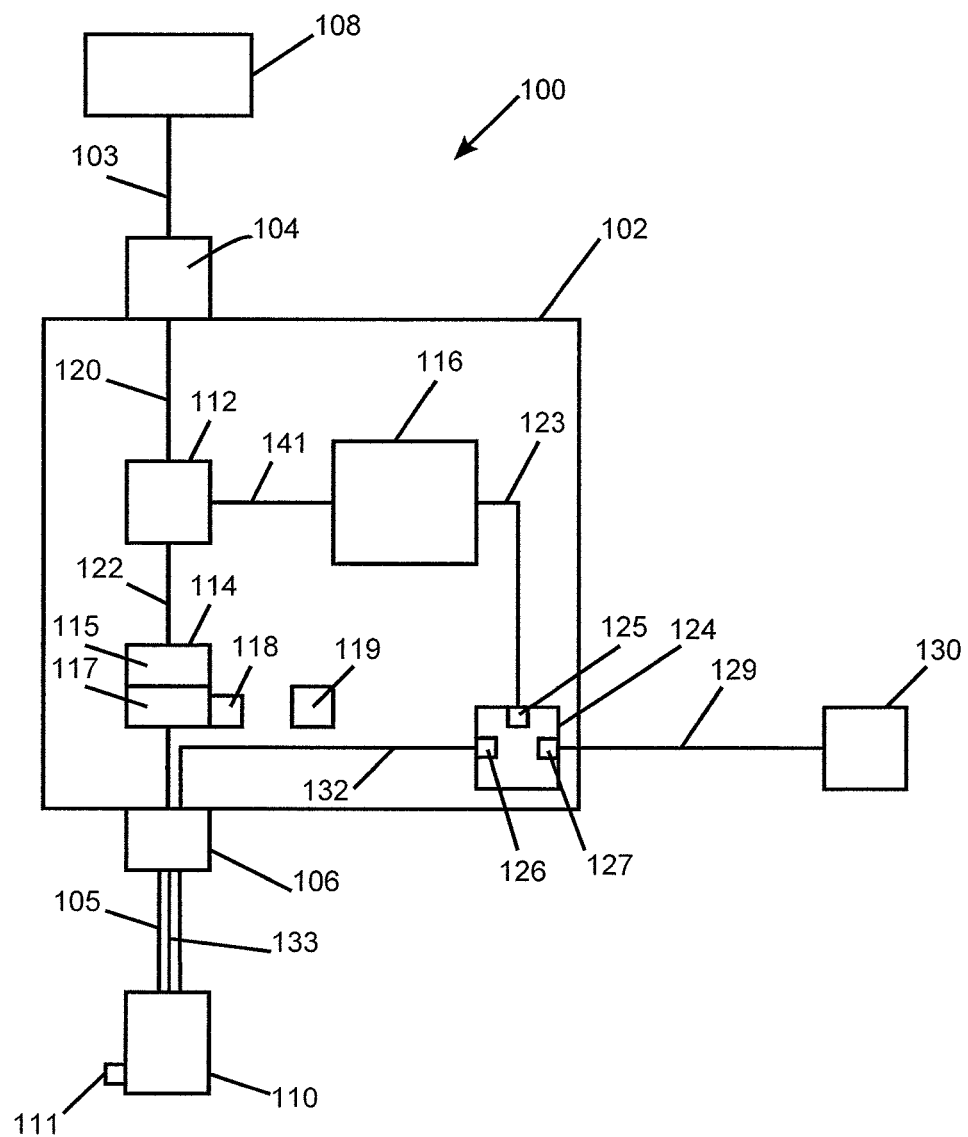
FIG. 2 shows a schematic view of an embodiment for remotely controlling a central vacuum source.

FIG. 2 discloses embodiment 100 of a device for remotely controlling a medical vacuum source. Embodiment 100 comprises housing 102, outlet port 104, and inlet port 106. Housing 102 is made of metal. The metal surface is non-porous and thus easily disinfectable. Other materials such as plastic may be used to construct housing 102. Outlet port 104 contains an adapter for creating an airtight connection to standard vacuum tubing 103 and connecting to vacuum source 108. Outlet port 104's adapter forms an air-tight seal through compressively engaging with tubing 103. Similarly, inlet port 106 contains an adapter for creating an air-tight seal with standard tubing for connecting to medical suction apparatus 110. A Luer-Lock or other style adapter may alternatively be used for the inlet and outlet port adapters.

Embodiment 100 contains activatable valve 112 arranged within housing 102. A first end of valve 112 connects to outlet port 104 through tube 120. Valve 112 is connected to controller 116 through control line 141, which controls the extent valve 112 is open. Activatable valve 112 is a solenoid valve such as Ingersoll-Rand Solenoid Valve Model #CAT66P-120-A. Other activatable valves may be used. The second end of valve 112 connects to filter 114 through tube 122.

Filter 114 is a multilayer filter, containing layer 115 for odor absorption and layer 117 for particle absorption. Odor absorption layer 115 contains activated charcoal and the particle absorption layer 117 is a ULPA filter. Filter 114 contains RFID tag 118. RFID tag 118 is a passive RFID tag containing embedded information indicating the filter type and lifetime. RFID transceiver 119 is arranged within the housing and oriented to read RFID tag 118. RFID transceiver 119 is a Melexis part #MLX90109 RFID transceiver, however, other RFID transceivers may be used.

Controller 116 is an Alterra Stratix FPGA; however, other FPGA's, microcontrollers, CPUs, or logic devices may be used. Controller 116 contains embedded software which controls the operation of controller 116. Controller 116 receives input from line 123 which is connected to output 125 of receiver 124. Controller 116 contains an internal timer.

Receiver 124 is a current sensor having output 125 and input 126. Receiver 124 has terminals 126 and 127. Terminal 127 is connected to external power supply 130 through wall socket plug 129 and terminal 126 is connected to power line 132. The voltage on output 125 is a function of the magnitude of the current passing through terminals 126 and 127. Receiver 124 is an isolated hall-effect sensor such as those offered by Allegro Microsystems, Inc. Alternative current sensors, such as a simple resistor voltage divider, may also be used. An analog to digital converter may need to be placed between receiver 125 and controller 116 depending upon the type of receiver and controller used. Receivers based on technology other than current sensors may also be used as will be described in the following embodiments.

Power line 132 connects to line 133, which passes out inlet port 106 and travels within tubing 105 to medical apparatus 110. Line 132 and 133 contain multiple wires including at least a ground wire and a power wire. In the following example, medical apparatus 110 is an electrosurgical device. Medical apparatus 110 contains activation button 111 for turning on the electrosurgical device.

The operation of the device 100 begins with properly connecting the device 100 to power supply 130, vacuum source 108, and medical apparatus 110. Wall socket plug 129 should be inserted into standard electrical wall outlet. Tubing 103 should be connected to the adapter of outlet port 104 and vacuum source 108, ensuring that air-tight seals are created. Tubing 105 similarly should be connected to the adapter of inlet port 106 and the suction port on medical apparatus 110. Also, line 133 should be connected to the power line 132 and medical apparatus 110.

After all the proper connections are made, the medical apparatus should be off (activation button 111 should not be depressed). Since the medical apparatus is not on, there will be no current flow through lines 129 and 132. The lack of current flow will be sensed by current sensor/receiver 124 and indicated on output 125. Controller 116 will read output 125 and determine that the medical apparatus is not on. Controller 116 will then send a command signal along control line 141. Activatable valve 112 receives the control signal along line 141 and shuts the valve closed. With valve 112 closed, fluid flow is prevented along the path from medical apparatus 110, into inlet port 106, through filter 114, through valve 112, out outlet port 104, and to vacuum source 108.

When a user of medical apparatus 110 depresses activation button 111, medical apparatus begins to draw current along line 133 and thus along lines 132 and 129. Current sensor/receiver 124 senses the increase in current flow through terminals 126 and 127, and thus changes the voltage on output 125. Controller 116 senses the change in signal on line 123 and in response changes the command signal on command line 141 from a closed signal to an open signal. Valve 112, in response to the open signal opens. Fluid is now allowed to flow from medical suction apparatus 110, and into inlet port 106. Impurities such as smoke particles and odors in the fluid coming in inlet port 106 are removed by filter 114. Fluid flow continues through valve 112, out outlet port 104 and into vacuum source 108.

Figure 3:
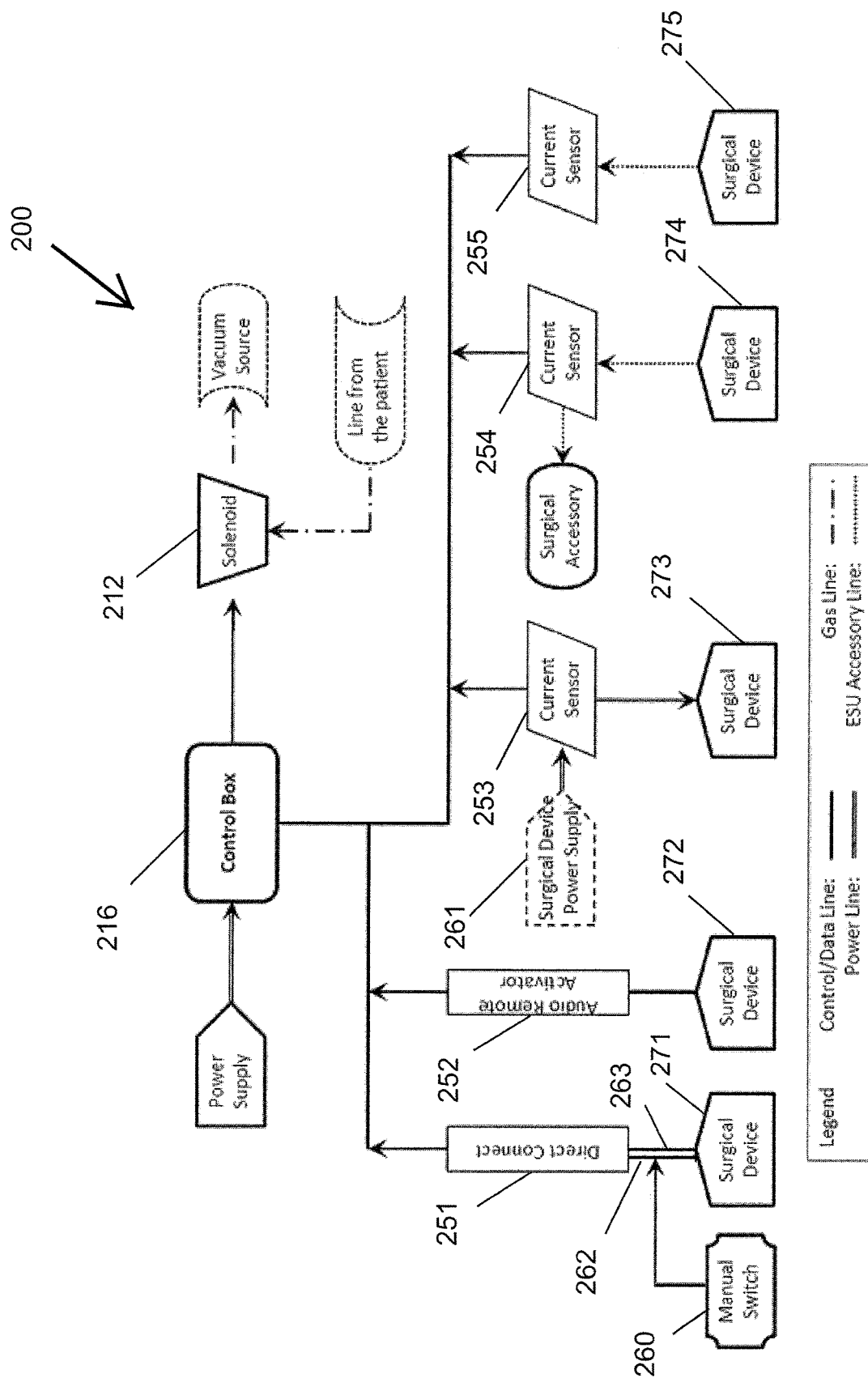
FIG. 3 is another embodiment for remotely controlling a central vacuum source.

FIG. 3 discloses an embodiment 200 which contains multiple receivers, 251, 252, 253, 254, and 255, designed to work with various surgical device types 271, 272, 273, 274, and 275. The multiple receivers allow for remote control to be accomplished in several different ways.

Receiver 251 is an adapter giving a direct electrical connection to manual switch 260 or surgical device 271. For example, manual switch 260 may be a foot pedal switch. Similarly, surgical device 271 may include manual switch buttons. Manual switch 260 and the manual button in surgical device 271 will electrically connect control wires 262 and 263. This electrical connection notifies the control box when the activation button on surgical device 271 or manual switch 260 are depressed and controls solenoid valve 212 accordingly. Alternatively, the manual switch or surgical device buttons may be analog switches which control an analog voltage level on line 263. In another form, the manual switch or surgical device buttons may provide a serial digital signal indicating their state on line 262.

Receiver 252 is an audio receiver such as a microphone. Surgical device 272 emits a fixed frequency tone when in use. Control box 216 contains a microprocessor for analyzing the microphone signal from receiver 252. Whether surgical device 272 is on is determined by analyzing the microphone signal. More specifically, a fast fourier transform is performed on the microphone signal. If the power within the frequency range containing the tone frequency emitted by surgical device is above a threshold, surgical device 272 is determined to be on and valve 212 is controlled accordingly. The threshold may be adjusted to minimize false activations. Additionally, DSP processors and advanced algorithms such as FIR and IIR filters may be used within the control box to more accurately trigger off of surgical device 272.

Receiver 253 is a current sensor connected to surgical device 273's power supply 261. Receiver 253 contains an output indicating the magnitude of the current drawn by surgical device 273. Control box 216's microprocessor compares the current level from current sensor (receiver) 253 and if determines if surgical device 273 is on based on whether the current sensor output exceeds a threshold. Multiple thresholds are used to detect multiple activation schemes of surgical device 273 and to adjust valve 212 accordingly. For example, surgical device 273 may be an electrosurgical device having a cut mode and a coagulate mode, each drawing different levels of current. A threshold may be created for each mode, and valve 112 assigned a separate flow rate for each mode.

Receiver 254 is a current sensor which operates without direct contact. Such current sensing is achieved using a hall-effect sensor or a sensor containing an electrical loop around the surgical device power line. Similar to the operation of receiver 253, depending upon the magnitude of the output from current sensor 254, control box 216 will appropriately adjust valve 212.

Receiver 255 is an RF sensor configured to measure an AM signal in the frequency range of 350 kHz to 1.25 MHz. RF sensor 255 may be coupled to an antenna. Receiver 255 is configured to detect the RF given off by surgical device 275 when in operation. For example, an electrosurgical device typically gives off amplitude modulated radio signals in the range of 350 kHz to 1.25 MHz. Control box 216 can perform signal analysis on receiver 255's output similar to the analysis performed on audio receiver 252's output. RF mixers may be used to convert the RF signal to a lower (baseband) frequency range which can be more easily analyzed by the microprocessor within control box 216.

Figure 4:
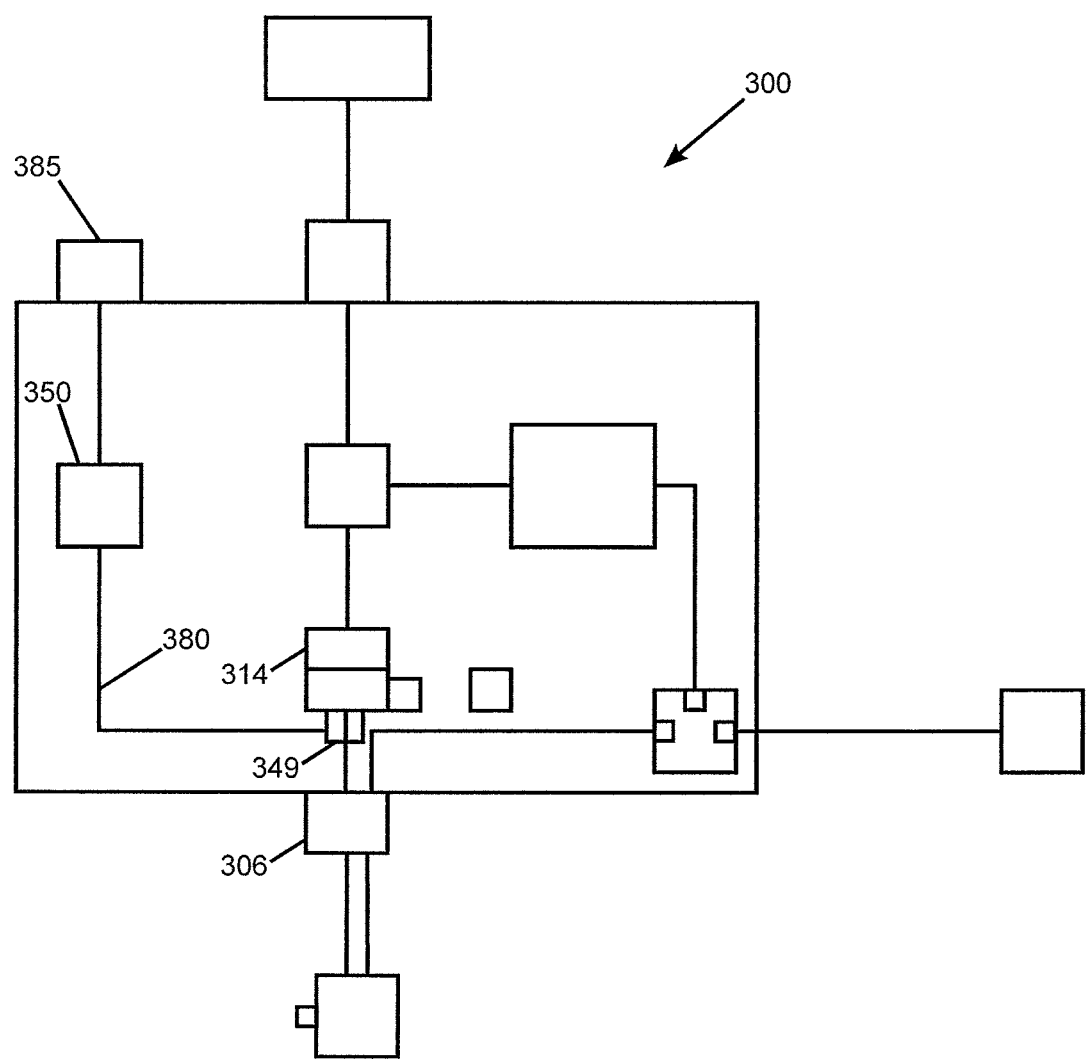
FIG. 4 is another embodiment for remotely controlling a central vacuum source with a flow splitter and a fluid canister.

The embodiment in FIG. 4 includes a flow splitter 349 and fluid canister 350. Flow splitter 349 is configured to separate any liquid entering inlet 306 into liquid path 380. The alternate path for gas should be free of any liquid. Flow splitter 349 may be part of filter 314. Fluid canister 350 may optionally be connected to liquid outlet port 385 which connects to an external liquid drain.

In other embodiments, a delay may be added to before switching the activatable valve open or closed from when the surgical device turns on and off. Additionally, a biohazard sensor may be added to any of the embodiments and may connect to an alarm. The filter may be designed to remove moisture. Additionally, an occlusion sensor may be added in the flow path and configured to cause the controller to shut the valve if an occlusion is detected. For example, if the suction device were to come into direct contact with flesh. Swivels may be added to the tubes. The device may be made of disposable or recyclable components. Additionally, the device may contain its own vacuum unit.

Figure 5:
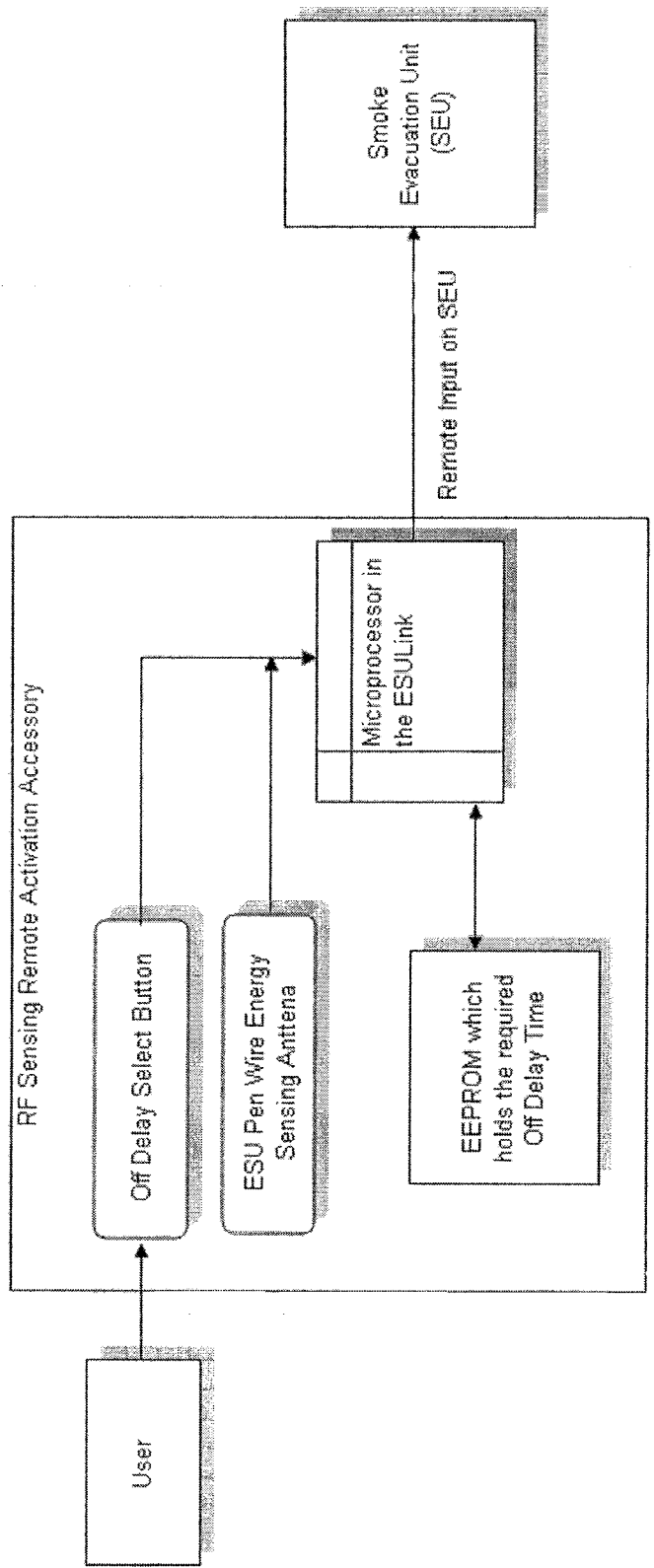
FIG. 5 is a layout of an embodiment with a remote control unit accessory.

In FIG. 5, a remote control unit for use with a filtration device is shown. This embodiment provides a remote control unit in an accessory format that can be used to remotely switch on and off any device through a controlled output wire. As shown in FIG. 5, a smoke evacuator unit is the controlled device, receiving the output wire from the remote control unit. This embodiment contains an RF sensor which is optimized for sensing the RF given off by an electrosurgical unit (electrosurgical pen). A user interfaces with the remote control unit in order to set a variety of operating parameters.

Figure 6:
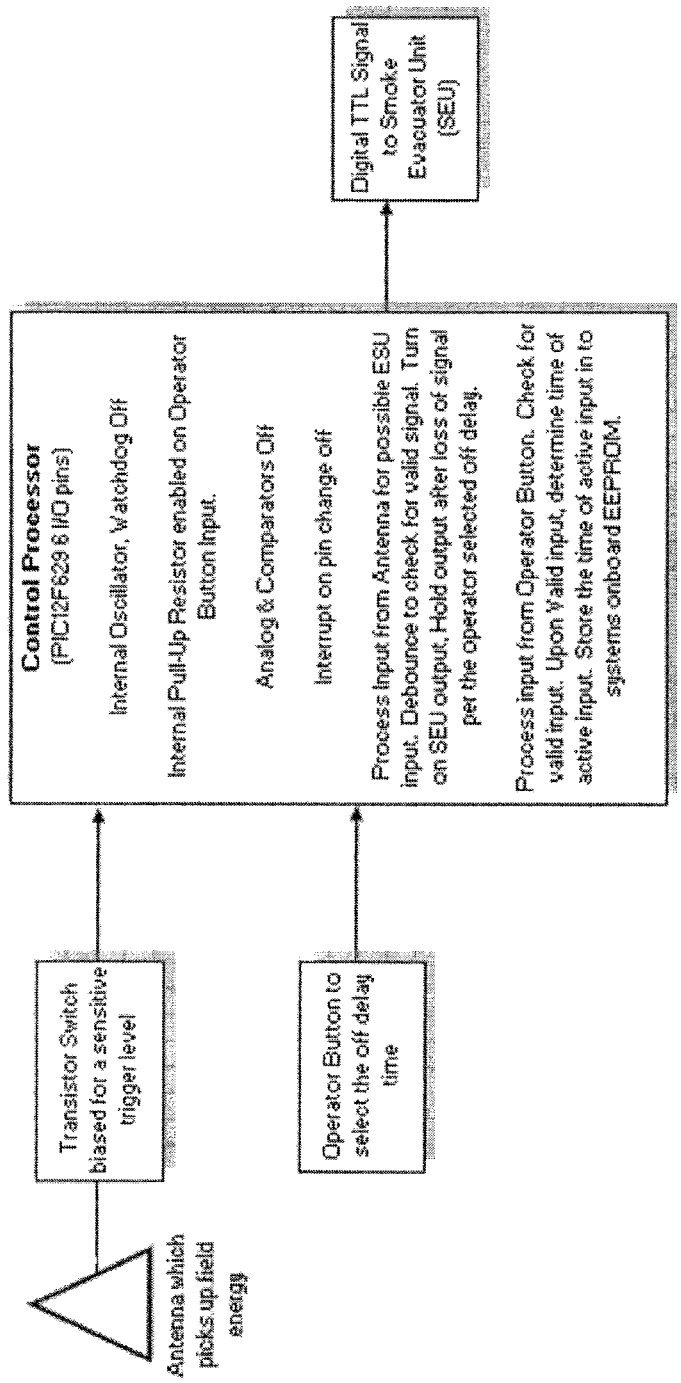
FIG. 6 is a high level circuit schematic.

FIG. 6 shows the major circuit elements of the remote control unit, including an RF antenna, an amplification transistor, a user button, a microcontroller, and the control output line. The RF antenna is embedded into a printed circuit board. The transistor is properly biased with a voltage divider such that an RF signal sensed by the antenna is amplied at the microcontroller input pin. Software is provided on the microcontroller which samples the amplified RF input from the transistor and sets the control output voltage as a function of the input signals and several configuration parameters.

Figure 7:
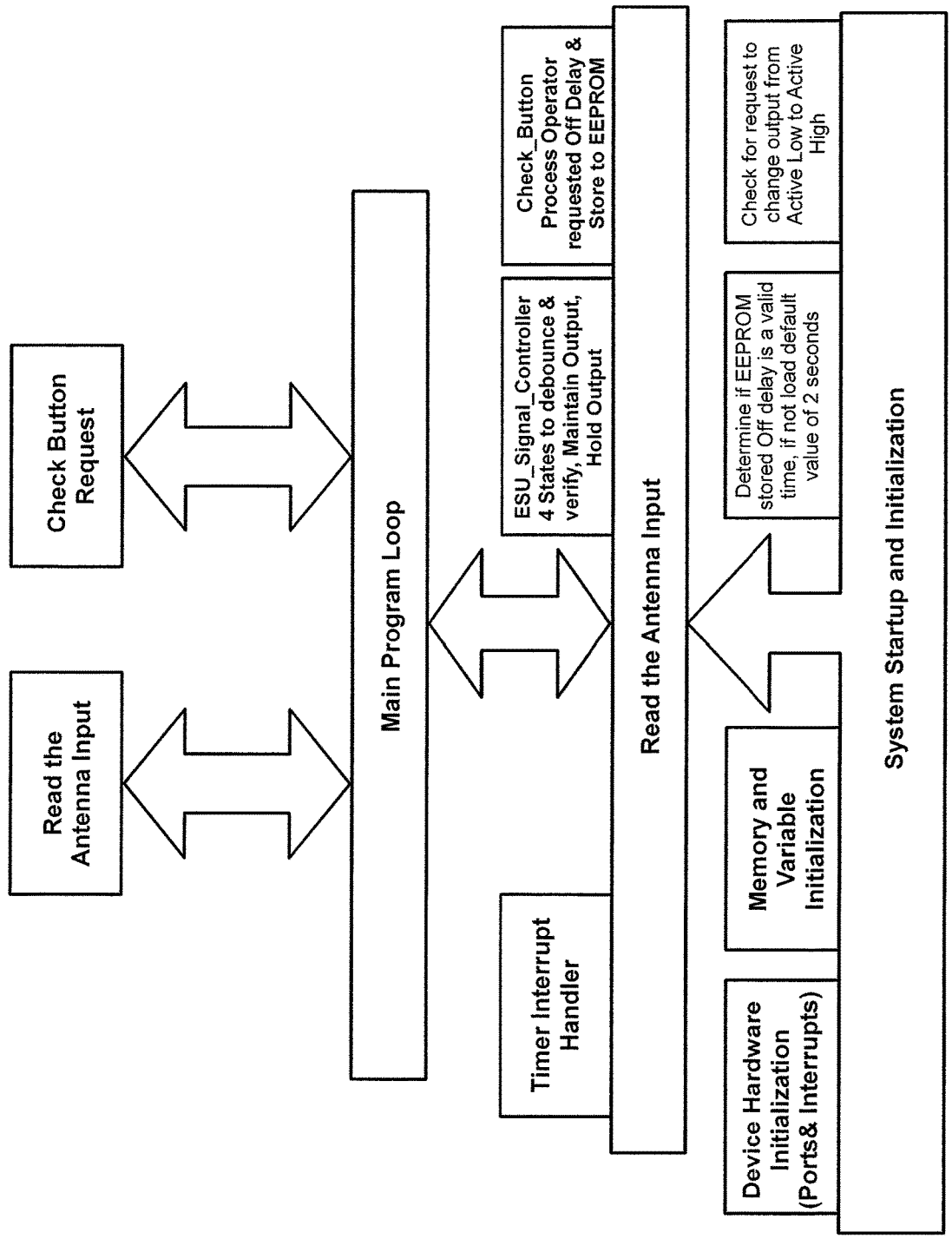
FIG. 7 is a high level software block diagram of the software running on a microcontroller.

FIG. 7 is a top level software block diagram of the software running on the microcontroller. Several interrupt driven program subroutines are used. One subroutine periodically samples the RF input and another subroutine determines the user button state.

In one aspect, a device can be triggered off of the radio signals emitted by a surgical device. Such triggering allows the remote control device to be electrically isolated (no direct wire contact) from the surgical device. Such a configuration is advantageous to ensure that the electrical system of the surgical device is not compromised by external systems, thus increasing safety. Also, a remote activation device is provided which can be remotely triggered off of a variety of signal types. For example, when the surgical device the embodiment is used with provides a direct electrical connection for triggering the remote device, an adapter for receiving such signal directly is provided. Alternatively, if the surgical device emits an audio signal during use, this audio signal can be used to trigger the remote device. In other scenarios, the radio frequency radiation emitted by a surgical device can be used as a trigger.

Therefore, while the presently-preferred form of the filtration device and system have been shown and described, and several modifications discussed, persons skilled in this art will readily appreciate that various additional changes may be made without departing from the scope of the invention disclosed herein.

What is claimed is:

1. A filtration system, comprising:
   a central vacuum source operable to provide constant suction;

medical tubing for carrying fluid generated during a medical procedure, said medical tubing in fluid communication with said central vacuum source;

a removable filter for removing contaminants from said fluid, said removable filter adapted to receive said fluid from said medical tubing, wherein said removable filter is positioned at least partially within an operating room wall such that contaminants are not discharged into said central vacuum source;

a fitting configured to fluidly connect said removable filter and said central vacuum source;

a flow control valve positioned between said removable filter and said fitting, said flow control valve operable to variably limit fluid flow to said central vacuum source;

an oxygen sensor adapted to determine $O_2$ concentration at a surgical site; and a control unit configured to control said flow control valve to adjust flow from the surgical site through said flow control valve as a function of said $O_2$ concentration.

2. The filtration system of claim 1, wherein said control unit is configured and arranged to remotely control flow through said flow control valve.

3. The filtration system of claim 1, further comprising:
a filter receiver positioned at least partially within said operating room wall for removably receiving said removable filter.

4. The filtration system of claim 1, wherein said flow control valve is a solenoid valve.

5. The filtration system of claim 1, further comprising:
an electrosurgical device in fluid communication with said medical tubing.

6. A remotely controlled filtration system, comprising:
a central vacuum source configured and arranged to provide suction for removing surgical smoke generated at a surgical site, said central vacuum source having variable suction and said central vacuum source having a maximum available suction;

a removable filter for removing contaminants from said smoke, said removable filter having a predetermined filter life;

a filter life timer for determining remaining filter life;

a fitting adapted for connection to said central vacuum source, said fitting positioned between said removable filter and said central vacuum source;

a remotely activated flow control valve positioned between said removable filter and said fitting, said flow control valve operable to variably limit a flow of fluid therethrough;

an oxygen sensor adapted to determine $O_2$ concentration at said surgical site; and a receiver operable to control said flow control valve to adjust flow from the surgical site through said flow control valve as a function of said $O_2$ concentration;

wherein said filter life timer is adapted to adjust said remaining filter life as a function of a percentage of said maximum available suction actually employed by said central vacuum source.

7. The filtration system of claim 6, further comprising:
an electrosurgical device in fluid communication with said central vacuum source.

8. The filtration system of claim 1, the control unit further comprising an audio receiver operable to detect a tone emitted by an electrosurgical device, wherein said audio receiver is operable to control flow through said flow control valve, and wherein said audio receiver comprises a microphone operatively associated with a microprocessor for analyzing a signal from said microphone.

9. The filtration system of claim 8, wherein said tone emitted by said electrosurgical device is at a fixed frequency.

10. The filtration system of claim 7, wherein said receiver comprises a current sensor operable to detect a current to said electrosurgical device without direct contact with a power line connected to said electrosurgical device.

* * * * *